United States Patent [19]

Lee

[11] Patent Number: 4,750,830

[45] Date of Patent: Jun. 14, 1988

[54] METHOD AND APPARATUS FOR MONITORING BLOOD-GLUCOSE CONCENTRATION BY MEASURING FOCAL PROPERTIES OF THE EYE

[76] Inventor: Arnold St. J. Lee, 1033 Hilts Ave., Los Angeles, Calif. 90024

[21] Appl. No.: 803,125

[22] Filed: Nov. 29, 1985

[51] Int. Cl.[4] .................. A61B 3/10; G01N 33/48
[52] U.S. Cl. .................. 351/211; 351/221; 356/39
[58] Field of Search .................. 351/205, 211, 221; 128/633; 356/39

[56] References Cited

U.S. PATENT DOCUMENTS 3,963,019 6/1976 Quandt .................. 351/39 X

Primary Examiner—Rodney B. Bovernick
Attorney, Agent, or Firm—Spensley Horn Jubas & Lubitz

[57] ABSTRACT

Optical power of a living subject's eye is measured and compared with a calibration value that corresponds to a reference blood-glucose level. The reference level is determined conventionally, as by blood analysis. Optical power of the eye increases with blood-glucose level. The comparison can include interpolation or extrapolation from two or more calibration points. Optical power is measured by projecting an image through an external optical system and through the cornea and lens of the subject's eye onto the subject's retina—while monitoring sharpness of focus at the retina, and systematically modifying the conditions of projection of the image. The relation between sharpness and projection conditions provides the measure of glucose concentration. For example, for presbyopic subjects, (1) the optical power of the external system may be varied, and the value of power that produces sharpest retinal focus may be used as the measure, or (2) the power may be held constant while the object distance is varied, and the distance that yields sharpest focus may be the measure. As another example, in nonpresbyopes the shortest or longest distance at which a subject can sharply focus may serve as the measure; this may be found by fixing the optical power of the external system and varying the object distance.

33 Claims, 2 Drawing Sheets

Fig. 2
a. NONASTIGMATIC EYE
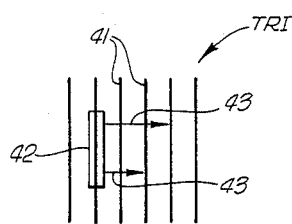
b. ASTIGMATIC EYE
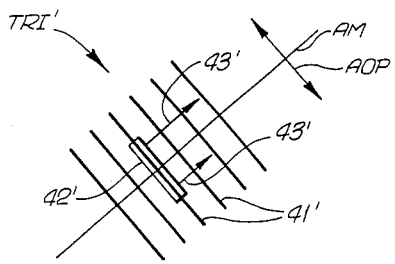
Fig. 3
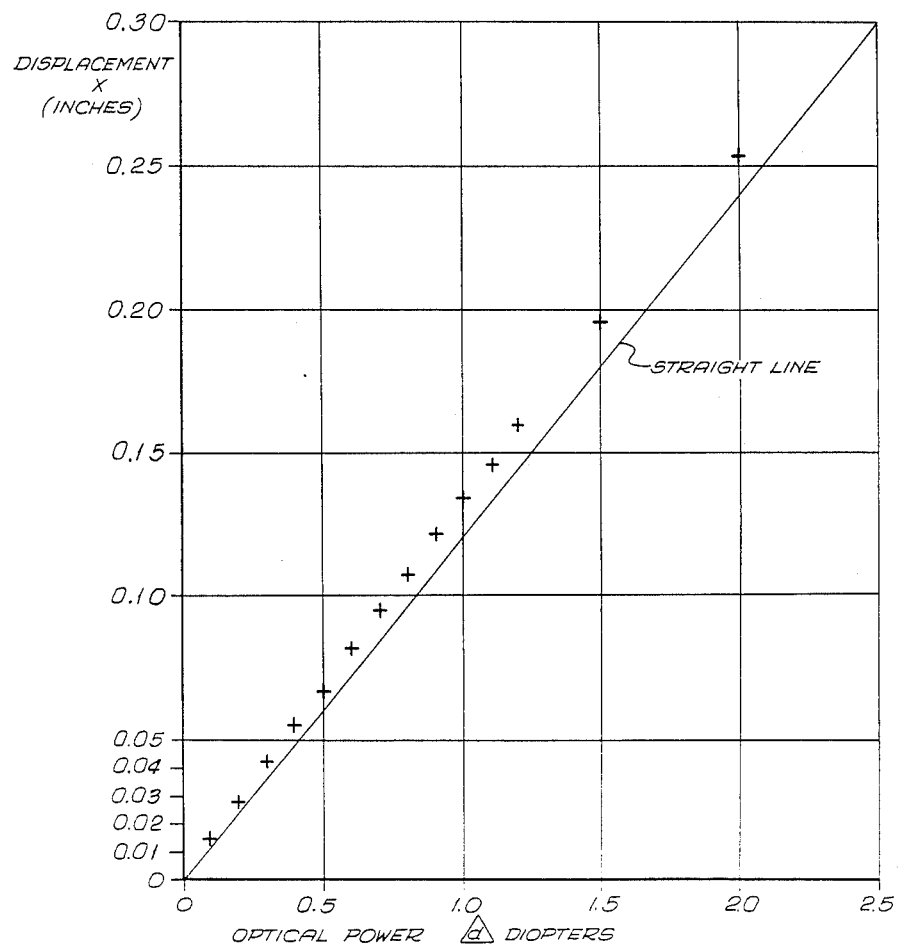

METHOD AND APPARATUS FOR MONITORING BLOOD-GLUCOSE CONCENTRATION BY MEASURING FOCAL PROPERTIES OF THE EYE

BACKGROUND

1. Field of the Invention

This invention relates generally to monitoring the medical condition of a living subject, and more particularly to novel methods and apparatus for noninvasive monitoring of blood-glucose concentration.

The invention is particularly intended for human subjects, but veterinary applications are also within the scope of my invention.

2. Prior Art

Effective diagnosis and treatment of various medical conditions requires a continuing sequence of information about the concentration of glucose in the blood. For example, patients with diabetes mellitus should tailor their diets and insulin dosage, if needed, to their blood-sugar levels.

For many such purposes average or mean values are preferable to instantaneous values, since the latter may reflect very brief fluctuations that are not significant or that could be misleading if used as a basis for treatment.

Ideally, average or mean glucose-concentration measurements should be available on short notice, at low cost, and as frequently as once or twice a day.

Present methods of monitoring the concentration of glucose in the blood of a living subject, however, require withdrawing a sample of blood and analyzing the sample chemically. The process of taking and analyzing a blood sample is not simple, is moderately expensive, is rarely done continually, and provides only instantaneous values.

There is another area of prior art that is relevant to my invention, although it has not heretofore been given a practical use in connection with blood-glucose measurement. It is well known to ophthalmologists that the eye is slowly responsive to the level of glucose in the blood. Abnormally increasing blood glucose causes the focus of the eye to shift toward the patient.

For example, if an old person, with no control over the accommodation (i.e., focus) of her or his eyes, happens to have far vision focused at infinity when that person's blood sugar is normal, the focus will shift to perhaps three feet—causing blurring of distant objects—with increasing abnormal blood sugar.

Because this effect is slow it is not responsive to short-term changes, but integrates blood-sugar content over a time period of about a day.

Yet another relevant area of prior art that has not heretofore been connected with blood-glucose measurement is the general field of optometry. Highly refined methods and apparatus are available for measurement and analysis of vision as such—but, as is well known, the purpose of optometry is to obtain information for correction of vision itself, rather than information for diagnosis or treatment of any other condition.

OBJECTIVES OF THE INVENTION

Primary objectives of my invention are to provide quick, easy and inexpensive mean blood-glucose measurements that do not require withdrawal of a blood sample and that can be performed even while the patient is at home.

For those patients who are not alert or mechanically inclined, another objective of my invention is to provide such measurements without active participation by the patient.

BRIEF SUMMARY OF THE DISCLOSURE

I have invented an instrument and a process whereby an untrained person can noninvasively measure and thus control his or her blood glucose expeditiously.

The process is to measure the blood glucose by determining the change in the "optical power" of the patient's eye optical system, and may also include using that information in planning the patient's diet, medication or personal habits, or any combination of these.

The apparatus is a device that projects an image, preferably with sharp boundaries (say a Ronchi ruling) upon the retina of the patient. The projection conditions or parameters of the instrument are variable. The instrument may also have some arrangement for determining the sharpness of the retinal image, or this function may be provided by the visual sensation of the patient himself. Any of several projection parameters of the instrument may serve as a measure of blood glucose.

More precisely, my invention provides a method of obtaining information related to blood-glucose concentration in a living subject. The method includes the steps of obtaining a test measure of the optical power of at least one eye of the subject, and then comparing the test measure with a calibration measure of optical power, to obtain the glucose-related information. The calibration measure corresponds to a reference blood-glucose level in the subject.

While this is the fundamental method of my invention, several variants are particularly important and may be mentioned at this point. First, the method may also include the steps of obtaining the calibration measure of optical power and determining the reference blood-glucose level in the subject. These steps are carried out substantially contemporaneously with one another, but generally before the step of obtaining the test measure. The step of determining the reference level may include analysis of the patient's blood.

Further, the "comparing" step may include noting whether the test measure is higher or lower (in terms of optical power) than the calibration measure. In this case, the glucose-related information that is obtained includes the conclusion that the patient's blood-glucose level is, respectively, higher or lower than the reference level.

(The validity of this last statement depends upon the understanding, which is to be observed throughout this document unless otherwise specified, that the test measure is considered in terms of optical power. This convention is adopted for definiteness since, as will become clear, actual numerical values used as indicia of the test and calibration measures may increase in either direction—depending upon the particular parameter monitored and the arbitrary selection of scale for the readout device employed.)

Also, the method may be performed with a reference level that is unhealthfully high, in which case the comparing step advantageously includes noting whether the test measure is or is not lower (again, always considered in terms of optical power) than the calibration measure. In this case, the glucose-related information includes the conclusion that the patient's blood-glucose is or is not, respectively, improved relative to the unhealthfully high reference level.

It will be understood that the calibration measure establishes only one point on a blood-glucose concentration scale. Since the amount of change in optical power per unit of change in blood-glucose concentration varies from one subject to another, the calibration measure cannot establish the scale expansion. Truly quantitative estimates of concentration therefore cannot be obtained from a single calibration measure.

On the other hand, it should also be understood that a typical scale expansion can be assumed for any given subject, and the calibration measure can be used to place the subject's response correctly on the scale at one point. The scale will then be at least roughly correct at other points, particularly at points near the calibrated point. In these cases the glucose-related information obtained may be regarded as loosely quantitative or semiquantitative Next, the comparing step may include comparing the test measure with not one calibration measure but a plurality of calibration measures of optical power—corresponding to a respective plurality of reference blood-glucose levels in the subject. In this case the glucose-related information includes a more quantitative estimate of blood-glucose concentration in the subject. The estimate is calculated from the plurality of calibration measures, the corresponding plurality of reference levels, and the test measure.

Still with reference to the principal variants of my novel method, the test-measure-obtaining step preferably includes these four substeps:

(1) projecting an image through an external optical system, and through the cornea and lens of the subject's eye, onto the subject's retina;

(2) during the projecting step, monitoring the sharpness of focus of the image on the subject's retina;

(3) during the monitoring step, modifying the conditions of projection of the image and determining the relationship between the projection conditions and the sharpness of focus; and (4) using the relationship to obtain the test measure.

I wish to emphasize that in implementing the method of my invention and its principal variants as described above, a great number of different specific detailed procedures may be used.

In particular with regard to the conditions of projection in the third substep mentioned just above, any of several different parameters of the external optical system may be varied to modify the conditions of projection, and thus may be part of the relationship between the conditions of projection and the sharpness.

Thus any of these various parameters may serve as the test measure of optical power of the subject's eye, as will be set forth in the detailed description that follows.

Now as to the apparatus of my invention, it is apparatus for obtaining information related to blood-glucose concentration in a living subject who has at least one eye that includes a lens and a retina. This apparatus includes some means for projecting an image through an external optical system and through the eye lens onto the retina. For purposes of speaking generally, this part of the apparatus will be called the "projecting means."

The projecting means operate under adjustable projection conditions (or in other words projection "parameters"), and the apparatus also includes some means for adjusting these projection conditions of the external optical system. This part of the apparatus will be called—again for purposes of generality—the "adjusting means."

The apparatus also includes an indicator, responsive to the adjusting means, for indicating the approximate blood-glucose concentration in the subject that corresponds to the projection conditions of the external optical system. This indicator is preferably graduated in units of blood-glucose concentration.

The adjustable projection conditions utilized may include, for example, the optical power of the external optical system, or alternatively the effective distance of the object from the patient's eye lens. Other conditions (or parameters) may be substituted that provide a discriminator for the focal condition of the patient's eye.

Other forms of my invention that are of primary interest include provision for rendering insignificant any glucose-induced astigmatism in the patient's eye, and for optimizing the sensitivity of the measurement. These provisions will be discussed briefly at this point.

Not only overall optical power but also astigmatism of a subject's eye varies with blood-glucose level. Effects of the baseline component of astigmatism (that which is present at the reference level of glucose concentration in the subject's blood) can be eliminated by using a corrective lens that is similar to the patient's ordinary eyeglass lens. Since the two glycemia-induced variations (in overall optical power and in astigmatism) are not simply correlated, however, the glycemia-induced component of astigmatism can seriously interfere with the measurement of overall optical power and thus with the determination of glucose level.

In an embodiment of the apparatus of my invention that is particularly for use if the subject's eye is astigmatic, the "object" whose image is projected consists of a plurality of parallel lines that advantageously are aligned essentially perpendicular to the axis meridian of the glycemia-induced component of astigmatism for the particular subject's eye. The glycemia-induced component of astigmatism can then only introduce a variation in optical power along an axis that is parallel to the plurality of parallel lines of the object.

The resultant variation in blurring is then limited to longitudinal blurring of the extreme ends of the image lines, as distinguished from transverse blurring of the portions of the lines between the ends. It is the latter that naturally will be considered in evaluating the sharpness of focus at the retina. Sharpness of focus of the image onto the retina is thereby rendered substantially independent of glycemia-induced astigmatism differing from that which corresponds to the predetermined blood-glucose reference level. As to measurement sensitivity, it is useful to recognize that the pupil diameter of the subject's eye affects sensitivity in two ways. The pupil diameter of a subject's eye varies, as is well known, with illumination. At high light levels the pupil diameter is very small, leading to long depth of focus. Determination of optical power of the eye lens is rendered difficult under such circumstances, since the retinal image will be sharply focused for a considerable range of projection conditions surrounding the nominal-focus or best-focus condition. The ends of this extended sharp-focus range are relatively gradual and indistinct.

On the other hand, at low light levels the pupil diameter is very large, leading to use of the peripheral regions of the eye lens and consequently to the usual aberrations that are characteristic of such regions. Determination of optical power of the eye lens is difficult in these circumstances too, though for the opposite reason: the retinal image is not sharply focused for any projection condition, including the nominal- or best-focus condition.

In both of these extreme cases it is difficult to find the nominal-focus condition, and thus difficult to obtain the desired measure of blood-glucose level. These extreme cases are avoided by bringing the pupil diameter to an intermediate value, ideally about five millimeters for the normal adult human subject.

The method of my invention preferably includes determining and using for the individual subject the illumination level that produces this intermediate value of pupil diameter. Each particular apparatus of my invention preferably includes means for customizing the apparatus to the individual subject who will use the particular apparatus—by controlling the illumination level to a value that is determined to produce the optimum pupil diameter in the individual subject, and by using a spectacle lens.

In apparatuses of my invention that will be used by most subjects whose eye-pupil dilation capability is substantially normal to at least well beyond pupil diameters of five millimeters, the object is illuminated in the range of roughly two to ten candelas per square meter.

As in the case of the method of my invention, the apparatus may be embodied in any of a great number of specific forms—several of which are detailed below.

All of the foregoing operational principles and advantages of the present invention will be more fully appreciated upon consideration of the following detailed description, with reference to the appended drawings, of which:

BRIEF DESCRIPTION OF THE DRAWINGS

FIG. 2 is a group of two diagrams showing how sharpness of focus on the subject's retina can be determined automatically in nonastigmatic and astigmatic subjects.

FIG. 3 is a graph showing the relationship between optical power and readout in one embodiment of the apparatus of my invention.

DETAILED DESCRIPTION OF PREFERRED EMBODIMENTS

Figure 1:
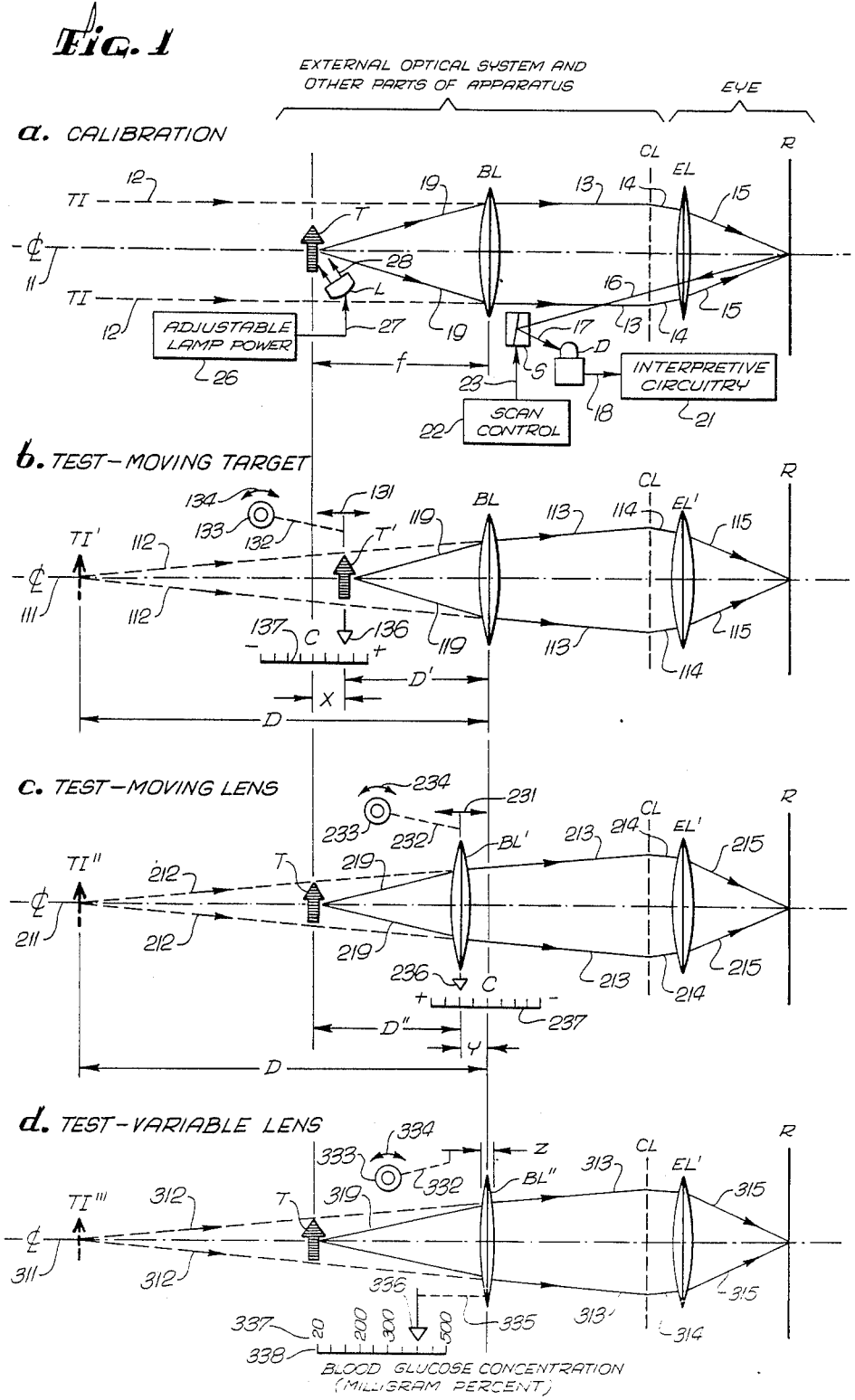
FIG. 1 is primarily a group of four related optical schematic diagrams showing generally preferred arrangements for practicing the method of my invention, and also showing preferred forms of the apparatus of my invention. In addition to the optical elements, FIG. 1 also includes in abstract block-diagram form a small number of electronic and mechanical components.

The procedure and apparatus of my invention have various embodiments for use with different types of subjects. First, in theory the form of the procedure depends on the subject's ability to substantially change the focus of the eye—that is, on whether the subject is presbyopic or nonpresbyopic. In practice, however, as will be seen the actual procedural manipulations are almost identical in these two cases.

Secondly, the form of the apparatus depends on the subject's sapience, competence and dexterity—that is, on whether the subject is a human being and able to think clearly and perform simple tasks with the hands and eyes. Depending on the subject's capabilities there is a corresponding range of equipment types, from fully manual and very inexpensive to fully automatic and relatively costly.

These points will be now be taken up in order.

If the subject is presbyopic, then in principle it is only necessary to determine the single value of optical power that the subject's eye can produce. As already explained, this can be done by finding the particular parameters of an external projection system that result in a sharp focus on the subject's retina—and then using those projection conditions as a measure of the eye's optical power, and thus as a measure of glucose concentration.

As a practical matter, however, in almost every case there will be some depth of focus of the eye. Regardless of the external apparatus used to determine sharpness of focus, therefore, near the point of nominal best focus the sharpness of focus will usually vary only slowly with changes of the external projection parameters.

Under these circumstances it will usually be necessary to find not one point but the two ends of the range of projection conditions that produce a generally sharp focus. These two points will produce two scale readings—or the equivalent in automatically collected data—which can be averaged to find a single value for use as the measure of glucose level.

Thus a human subject using a manual device may start at one end of the adjustment range of the device and slowly adjust the device through the range of adjustments at which the image appears sharpest, stopping and making a reading just as the image begins to blur again—and then adjusting the device in the opposite direction and again stopping for a reading just as the image begins to blur.

An automatic device for a presbyopic subject will perform virtually the same procedure, although with automatic equipment it is typically just as accurate to find the two ends of the sharp-focus region while moving continuously in one direction. Whether performed manually or automatically, this two-point procedure may be regarded as simply a procedure for finding the setting that maximizes the sharpness of focus.

In the case of automatic equipment it may be preferred to use one or the other of the two values taken singly as the measure, since automatic apparatus can identify a particular degree of blurring more reproducibly than can a human observer. The automatic device may be programmed to use either the "near point" or "far point" of clear vision as the glucose-level measure.

If the subject is nonpresbyopic, the subject of course can focus on objects at a great range of distances. In adult humans with normal vision or with a corrective lens, this range extends from infinity to less than ten inches. Such a subject is not only able to focus on any object in this range, but must exert a concentrated effort to avoid doing so when attention is drawn to such an object. Hence an absolute measurement of the optical power of the subject's eye is only meaningful at one or the other end of the subject's range of focus.

A suitable measurement strategy in accordance with my invention is to lead the subject's eye from focusing on an object that is readily within the focal range to an extremum of that range. At the instant when the subject's eye is no longer able to focus, the optical power of the eye may serve as a measure of glucose concentration.

Again, any of various projection parameters of the external optical system at that instant will provide an index to the optical power of the eye and thus the glucose concentration. Interestingly, among other available parameters, the distance itself at which the subject can no longer focus may serve as the measure of both optical power and glucose level.

I emphasize that for purposes of this document, phrases such as "a measure of the optical power of at least one eye of the subject" encompass measurement of the distance to the "near point" or "far point" of the subject's focal range.

The similarity of this measurement strategy for nonpresbyopic subjects to the procedure previously described now be noted. Although the underlying reasons are different, in both instances the external apparatus is adjusted from a projection condition that produces a fairly sharp focus until the image begins to blur, and the projection condition at that point is the measure of glucose level.

In fact, the presence of depth of focus is a factor in nonpresbyopes as well as presbyopes, but in nonpresbyopes depth of focus will normally (with suitable illumination) amount to only a slight extension of the already long focal range. Also, in the nonpresbyopic case as well as the presbyopic case, the "far point" of vision may be used as the focal-range "edge" where the measure is obtained; and for best reproducibility both the "near point" and "far point" may be used.

Now I will turn from the topic of presbyopia as it affects the method of my invention to the matter of the subject's ability to aid in making the measurement.

If the subject has the mental and physical capacity to operate a simple mechanical device while viewing an image, the ability to determine when an image is sharply focused, and the mental alertness to deal adequately with the information generated, then the apparatus of my invention can be a completely manual device. The apparatus can be, as an example, roughly the size and configuration of a small kaleidoscope. The subject operates a single control that varies a projection parameter, stopping when the image begins to blur, and reads an indicator pointer against a graduated scale.

As will be apparent, the pointer and scale can be replaced by a digital or other type of readout if desired. Further, the glucose-level readout can be in the form of instructions for medication or the like, rather than in terms of glucose level as such.

There are many circumstances under which such an apparatus will not be appropriate. At one extreme, the subject is not necessarily a human being: various animals may require treatment for disorders relating to glucose concentration. At another extreme, the subject may be an elderly person who is slightly feeble, or lacks manual dexterity due to neural disorder, or is slightly disorganized, and thus unable to make the measurement or use the resulting data appropriately. Between these extremes, the subject may be a person who is completely incapacitated, or senile, or infantile. Yet another possibility is that the subject may be a participant in a multiparameter medical screening program that monitors the patient's overall condition—one of the parameters being blood-glucose concentration.

In such cases the apparatus of my invention includes some means for automatically sensing sharpness of focus of the image on the retina.

At least for use with presbyopic subjects, the apparatus may also include some means for controlling the previously mentioned "adjusting means" to maximize the sharpness. By operation of these sensing and control means the apparatus automatically focuses the image on the retina to maximum sharpness—and then indicates the blood-glucose concentration level in the subject that corresponds to the projection conditions of the external optical system.

If the depth of focus in the subject's vision is too great for accurate location of the sharpest-focus point, then instead of means for controlling the adjustment to maximize the sharpness the automatic apparatus may include means for controlling the adjustment to progressively vary the adjustment from projection conditions in which the effective distance of the object is, for example, at infinity toward conditions in which the effective distance of the object is very small. Alternatively the effective distance can be varied in the opposite direction. Either or both of these can be accomplished by varying the actual object distance, or by adjusting the position or power of a focal element in the external optical system as will be shown.

With this form of the apparatus the automatic sensing means operate as before, depending upon the accommodation of the subject's eye to "follow the object in" until it is no longer possible to do so. The measure of glucose concentration is found from the projection conditions at the instant when the automatic sensing means determine that the retinal image is no longer sharply focused. As previously mentioned, this determination is to be regarded as one way of determining the optical power of the eye.

FIG. 1 shows, in the topmost portion titled "a. CALIBRATION," how to set up for practice of the method of my invention, and also the basics of construction of an apparatus according to my invention. The example illustrated will be most pertinent to use for a presbyopic subject with very short depth of focus, and that context will be assumed for the present.

The retina R and eye lens EL of the subject's eye appear at the right end of the drawing. The subject's eye is focused at infinity, either by virtue of the focal capability of the eye alone or (as will more commonly be the case for presbyopes) in combination with an ocular lens CL that is customized to the particular subject. A far-vision spectacle lens may be employed for this purpose and also for correction of baseline astigmatism.

Thus the retina R receives converging rays 15 from the eye lens EL, and these rays are derived from parallel rays 13 within the apparatus. If the unaided eye lens EL is unable to achieve this condition, then the custom ocular lens CL is present—and from the parallel rays 13 this custom ocular lens CL produces refracted rays 14 between the ocular lens CL and the eye lens EL. The inclination of these refracted rays 14 is such that the eye lens EL can focus them onto the retina.

The source of the parallel rays 13 is in turn an object or target T that is separated from an objective lens BL by the focal length f of that lens. By virtue of this spacing the objective lens BL functions as a collimator for rays originating near the axis 11 of the system; hence the parallelism of the rays 13. From the point of view of the eye, however, the rays 13 appear to be derived from a target image TI that is very far away. That is to say, the rays 13 appear to be continuations of rays 12 from a virtual image TI far behind the lens.

In principle all of the method and apparatus of my invention could be performed and constructed using a target actually far from the subject's eye, but in nearly all circumstances such a construction would be impractical because of the large dimensions involved. The objective lens BL functions primarily to bring the system to a practical overall size, though it can also be used to vary the projection conditions without moving the target, as will be explained shortly.

The target T is illuminated by light 28 from a lamp L, which in turn is supplied with power through wires 27 from an adjustable lamp power supply 26. This supply 26 is adjusted to bring the subject's pupil diameter to approximately five millimeters, and thereby to optimize the measurement sensitivity for depth of focus and for aberrations.

To set up the calibration point, the lens and target are separated by the proper distance f, and the sharpness of focus on the subject's retina is checked. This can be accomplished by, for example, the conventional technique of an optometrist—trying a variety of lenses CL while asking the subject which produces the sharpest or darkest appearance of the image. Alternatively the sharpness can be monitored by an assistant who actually looks through the subject's eye, and through a suitable intermediate lens, at the image on the retina.

An automated version of this same approach can be performed as suggested in FIG. 1, using a photodetector D and a photoelectric beam deflector or scanner S, energized through wires 23 by a scan control device 22. The sensitive area of the photodetector is focused by a lens (not shown) onto the retina, by way of the scanner S, and the scanner repetitively moves the image of the detector sensitive area across the image of the target on the retina. As the detector is sequentially exposed to light dark features of the target image, the sharpest focus can be identified by, for example, the most abrupt changes in detector signal on the signal path 18 to the interpretive circuitry 21.

In any event the sharpness of focus is checked to determine whether the subject with eye relaxed by a drug is able to focus on the target image TI at infinity, to produce the relationships diagrammed, without aid of an ocular lens. If so, no ocular is left in the apparatus; if not, an ocular CL is permanently installed that permits the subject to focus on the target image TI at infinity with drug-relaxed eye.

If the subject normally wears eyeglasses, the prescription in the eyeglass lens for the eye that is being checked will often serve as a close starting point for the custom ocular lens CL. Such an eyeglass lens will have not only very nearly the proper overall power, but will also have an astigmatism correction if the subject normally requires such a correction. The eyeglass lens is not likely to be exactly correct, however, since optometrists customarily bring their patients' best corrected vision to intermediate distances rather than to infinity, and also because the subject's glucose concentration at the time of calibrating the apparatus may be substantially different from its value at the time of fitting the eyeglasses.

As an alternative the subject may simply wear the normal eyeglasses, during performance of the method or use of the apparatus of my invention, and a custom ocular CL may be fitted to make any small residual correction as required. I consider this a relatively undesirable alternative because the eye is best positioned as close as possible to the instrument to maximize the apparent size of the field.

In any event, provision of a suitable custom lens CL if required, either alone or in combination with the subject's normal eyeglasses, frees the operation and condition of the rest of the apparatus from complicated dependence on the optical characteristics of the subject's eye. That is to say, the remainder of the apparatus can be essentially standard: the only variations required in calibration or configuration for use with different individual subjects will be in the readout scale and in the target orientation and illumination.

The positions and conditions of the target T, objective lens BL, and any other optical elements in the system constitute the projection conditions or parameters at calibration. Typically one or more of these conditions or parameters is selected for use as the measure of glucose level.

Whichever movable part of the apparatus is so selected is fitted with an adjustment mechanism and an indicator device. The indicator is set either (1) to "zero'-'—meaning zero deviation from the baseline value of glucose concentration—or preferably (2) to a reference numerical value of blood-glucose level that is measured in the subject by conventional methods.

Sections "b" through "d" of FIG. 1 illustrate three different ways of changing the projection conditions of the external optical system to provide a retinal image that can be focused—and thereby to determine, in effect, the optical power of the eye.

More specifically, if it is the actual position of the target T that is to be varied, then as suggested in the second section of FIG. 1, titled "b. TEST—MOVING TARGET," a moving pointer is provided that is controlled in common with the target (here identified as T'). A graduated scale 137 on the apparatus, adjacent to the path of the pointer 136, is adjusted as required to place the correct value under the pointer, so that the two together read correctly at calibration.

The scale is positioned either (1) with its zero or "calibration" point C, or (2) with the known numerical reference value, in alignment with the original calibration position of the pointer and target (position T in section "a" of FIG. 1). Examples of scales 137, 237 having merely zero or calibration points C, and positive and negative excursion indicia such as plus and minus symbols "+" and "−", appear in the second and third sections ("b" and "c") of FIG. 1. An example of a scale 337 having numerical-value indicia 338 appears in the fourth section "d") of the drawing. It is to be understood that either form of readout may be used in any of the three variant devices illustrated.

If it is the target that will move, then the target is mounted for adjustment longitudinally (i. e., parallel to the centerline 111) as suggested by the two-headed arrow 131, and it is connected by a mechanical linkage 132 to a control knob 133. The knob 133 is mounted for bidirectional rotation as suggested by the curved two-headed arrow 134. If preferred, the pointer 136 may be fixed to the knob 133 or its shaft (not illustrated) for rotation, and the scale 137 may be a circular-segment scale; or other types of readout may be provided.

After calibration, still assuming a presbyopic subject with very shallow depth of focus, if the subject's glucose level increases the eye will focus at a closer distance than initially. This occurs because the increased glucose concentration causes the curvature of the eye lens EL' to become sharper, and so to have increased optical power.

This condition is represented schematically by showing the eye lens EL' as a thicker lens, in the right-hand portion of the lower three sections "b" through "d" of FIG. 1. Here the eye is again focused at the only distance where it can be focused, but as suggested in the drawing if a custom ocular lens CL is present the rays 114/214/314 between that lens CL and the eye lens EL' will be at a different angle from the corresponding rays 14 in section "a" of the drawing. As a result the eye is no longer able to focus the rays 13 (section "a") apparently originating as by the dashed lines 12 from a target image TI at infinity, but now instead focuses rays 113/213/313 that are diverging—as from a virtual image TI'/TI''/TI''' that is much closer to the eye. It is to be understood that the foreshortening of focus has been exaggerated in the drawings of FIG. 1 to permit the illustration itself to be a convenient size. In actuality even the virtual image TI', TI'' or TI''' is too far from the eye to be presented in an apparatus of convenient size without an objective lens BL/BL'/BL''.

In section "b" the target itself is shifted as previously described, so that diverging rays 119 are refracted by the objective lens BL to follow path 113—whose extension, the dashed lines 112, diverges from the target image TI'—a virtual image. While the virtual image TI' has been shifted in from infinity to perhaps a few feet from the eye, the actual object or target T' has been shifted only by a matter of inches, or even a fraction of an inch. The distance through which the actual target has moved, from position T (section "a") to position T' (section "b") is represented as x in the drawing. This distance now is the measure of glucose concentration.

As shown, the position of the target is indicated by the pointer 136 on the graduated scale 137 as increasing toward positive values (the end of the scale marked "+") while the retina R has shifted away from the eye lens EL'—corresponding to an increase in blood-glucose concentration.

It is to be understood that the adjustable lamp power supply 26, lamp L, and automatic image-evaluation components S, D, 18, 21, 22, 23 of section "a" are also present in the apparatuses of sections "b" through "d," having been omitted from these latter drawings only for clarity of illustration.

In the third section of FIG. 1, titled "c. TEST—MOVING LENS," it is the objective lens rather than the target that is shifted. The lens is moved from the position BL of section "a" to the position BL' of section "c", to intercept the diverging rays 219 from the target T closer to the target, so that these rays 119 are refracted by the objective lens BL to follow path 213— which is substantially identical to (except that it is longer than) the path 113 of section "b."

The extension of the path 213 in section "c," namely the dashed lines 212, diverges from the target image TI''—again a virtual image, whose position is the same as that of the target image TI' in section "b." Here too, the virtual image TI'' has been shifted in from infinity by a very large increment, but the objective lens has been shifted only by a matter of inches, or even a fraction of an inch. The distance through which the lens has moved, from position BL (section "a") to position BL' (section "c") is represented as y in the drawing. This distance now is the measure of glucose concentration.

As shown, the position of the movable lens is changed in either direction—as indicated by the two-headed arrow 231—through a mechanical linkage 232 from a suitable control such as a knob 233, which can be rotated in either direction as suggested by the two-headed curved arrow 234. The instantaneous position of the lens BL' is indicated by the pointer 236, which is controlled in common with the lens position.

The pointer is read against the graduated scale 237 as increasing toward positive values (the end of the scale marked "+") while the eye lens EL' has become more strongly curved and therefore has acquired greater positive power—corresponding to an increase in blood-glucose concentration. This requires that the scale 237 in section "c" be laid out in the opposite direction to the scale 137 of section "b" (or that some intermediate reversing linkage be provided), since the motion of the lens BL must be in the opposite direction to the motion of the target T, to achieve the same focal condition at the eye.

In the fourth section of FIG. 1, titled "d. TEST—VARIABLE LENS," neither the objective lens nor the target is bodily shifted. Instead the optical power of the lens is itself changed. This change is symbolized in the drawings by showing the lens BL'' in section "d" as a thinner lens than the lens BL in section "a." In such a lens BL'' the curvature is also shallower than that of the lens BL. Various optical devices are available modernly that can produce an effect equivalent to changing the lens thickness and curvature—as, for example, a compound lens whose opposed surfaces shift with respect to one another.

With this type of device in place, as in section "d" of FIG. 1, the lens BL'' intercepts the diverging rays 219 from the target T at the same longitudinal position as does the lens BL in the calibration condition of section "a," but turns them refractively through a smaller angle than the lens BL of section "a"; hence these rays 219 are refracted by the thinner objective lens BL'' to follow path 313—which is substantially identical to the paths 113 of section "b" and (except for length) 213 of section "c."

The extension of the path 313 in section "d," namely the dashed lines 312, diverges from the target image TI'''—yet again a virtual image, whose position is the same as those of the target images TI' in section "b" and TI'' in section "a." Here as in the two preceding cases, the virtual image TI'' has been shifted in from infinity by a very large increment, but the power of the objective lens has been modified only by a very slight amount.

In terms of lens thickness, to continue this somewhat symbolic representation, the change is a very small fraction of an inch. The thickness of the lens is represented as z in section "d," and is symbolically shown as controllable through a mechanical linkage 332 from a control knob 333—which is rotatable in either direction, as suggested by the two-headed arrow 334.

Once again there is a pointer 336 controlled in common with the lens thickness z, as by a mechanical linkage 335, and this pointer is disposed to move along a graduated scale 338.

For purposes of example only, this scale 338 is shown as calibrated in glucose concentration values. One suitable scale that is already used in the field is "milligrams percent," which means the number of milligrams of glucose per hundred cubic centimeters of blood. The concentration scale may be nonlinear. Assuming the calibration point to have been taken at blood-glucose concentration of 150 milligrams percent, the pointer 336 on the graduated scale 337 is shown as moving toward higher values (that is, toward the end of the scale marked "500") while the eye lens EL' has become more strongly curved—corresponding to an increase in blood-glucose concentration.

With the foregoing description in mind we can now drop the assumption that the subject is presbyopic and has a very shallow depth of focus. It will next be assumed instead that the subject is presbyopic but has a significant depth of focus at the illumination level selected—a much more common condition. Now the calibration measure proferably entails finding not one but two positions for the target T, at which the image of the target T is just beginning to be defocused—by approximately the same amounts. If the blurring is very nearly the same at both points, then an average of the two readings will be very nearly the central or nominal best-focus condition. Since these measurements are made with the presbyopic eye focused at infinity—either with or without correction, as previously mentioned—the illustration of section "a" of FIG. 1 remains applicable.

Similarly after the subject's glucose level has changed (e. g., increased, as illustrated in FIG. 1), test measurement of the new optical power of the eye by any of the systems shown in FIG. 1 will require not one but two test measurement points—representing approximately equal blurring in both directions from the sharp-focus range—and averaging of the two indicator positions to find the central or nominal readout value. These measurements too are made with the presbyopic eye focused in its single available focal condition, but as shown this will no longer be at infinity. The drawings of sections "b" through "d" of FIG. 1 remain applicable under the present assumption that the presbyopic subject's depth of focus is substantial.

Now if the subject is assumed to be nonpresbyopic, the same general measurement strategy may be employed, but the optical power must be found at the subject's "near point" or "far point"—or both.

For calibration at the nonpresbyopic subject's "far point," the diagram in section "a" of FIG. 1 continues to be appropriate. At the "near point," however, it will be understood that the eye is not focused at infinity as shown. Therefore section "a" of FIG. 1 is not applicable to calibration conditions at the "near point" for nonpresbyopes.

Instead, the drawings of sections "b" through "d" of FIG. 1 may be taken as representing both the calibration and test measurement conditions. In both calibration and test at the "near point," rays from the virtual image of the target are diverging, but the precise amount of divergence will depend upon the glucose level.

For example, if the moving-target system of section "b" is used, and if the position T' of the target is obtained in calibration, the scale 137 may be moved so that the central point "C" is aligned with the pointer 136. A conventional measurement of blood-glucose concentration is made, and associated with this center-scale indication. Displacements from this center point will then represent glucose-concentration changes from the reference level.

With some subjects it will be found preferable to use the "near point," and with others it will be preferable to use the "far point"; and with yet others, both. The distinctness of the near and far edges of the sharp-focus range will vary from one subject to another, so ideally the more distinct edge (if there is one) should be found for the particular subject at the time of calibration, and thereafter that same edge used for test measurements.

If neither edge is reasonably distinct, then both may be used. While it may not be considered physically meaningful to average infinity with a value of perhaps ten inches, nevertheless the two scale readings may be averaged to obtain an optical-power measure in arbitrary units that is somewhat more precise than either reading considered alone. Ophthalmologic distances are often measured in diopters (the reciprocal of the "metric" distance in meters). Averaging the dioptric distances is then reasonable in this case.

Even in cases where both edges are reasonably distinct, as well as in presbyopic patients where there is a substantial depth of focus as previously assumed, finding and averaging both ends of the sharp-focus range adds a check on thevalidity of the data.

The object or target T, T' of FIG. 1 advantageously may be a group of several parallel lines. When the eye is sharply focused on the target, this pattern will be reproduced on the retina to form a target retinal image such as TRI in FIG. 2, section "a," consisting of several parallel lines 41. If the subject's eye is nonastigmatic, and remains so even with changing blood-glucose concentration, the orientation of the lines 41 is immaterial and may be selected arbitrarily. (In fact, for such eyes the target need not be a group of parallel lines but may instead be any elaborate pattern.)

The same is true if the eye is astigmatic and the astigmatism remains substantially constant despite changes in glucose concentration. The astigmatism in this case can be disregarded for present purposes because the necessary constant correction can be provided by the custom ocular lens CL (FIG. 1).

If the eye is subject to astigmatism that varies with glucose concentration, however, the eye may be characterized as having an "axis meridian of glycemia-induced astigmatism." As is well known, astigmatism may be represented as a cylindrical lens in series with the eye, and the so-called axis meridian is essentially the axis of that cylindrical lens. The axis meridian AM of glycemia-induced astigmatism in a particular subject is shown in section "b" of FIG. 2. It is to be understood that the particular orientation of the axis meridian AM in this drawing is only arbitrarily selected for purposes of illustration, and in an actual subject may be at any angle to the vertical.

The additional astigmatic optical power produced by such a lens is of oourse not isotropic as in the case of a spherical lens but instead introduces a magnification in one direction only—namely, in the direction AOP (section "b" of FIG. 2) that is perpendicular to the axis meridian.

It is desirable to avoid the effects of this additional optical power AOP due to glycemia-induced astigmatism. Otherwise this additional optical power AOP may distort the overall change of optical power—making the determination less sensitive—and may otherwise confuse the determination of optical power that is described above.

To eliminate this possible confusion, the target pattern is advantageously rotated to bring the target retinal image to the orientation TRI' of section "b" of FIG. 2, in which the lines 41' are perpendicular to the axis meridian AM—and are parallel to the additional astigmatic optical power AOP. This adjustment will produce the sharpest apparent focus, for the following reason.

In this orientation, the glycemia-induced astigmatic optical power AOP will only blur the very ends of the lines 41', and only blur them longitudinally, thus having substantially no effect upon the sharpness of the long edges of the lines. It is to be understood that the sharpness of the long edges of the lines is the parameter that will be naturally be used in determining the image sharpness, whether by the subject's own visual sensation or by instrumentation.

As an alternative, if it is known for a given subject that the glycemia-induced astigmatic optical power is well correlated with the overall glycemia-induced optical power, the target pattern may be rotated to the orientation perpendicular to that shown in section "b" of FIG. 2—namely, with the lines parallel to the axis meridian, and perpendicular to the direction of glycemia-induced astigmatic optical power AOP. In this case the astigmatic optical power AOP will effectively add to the overall glycemia-induced optical power, rendering the measurement more sensitive.

For purposes of automatic instrumentation, the sensitive area of the detector D (FIG. 1 section "a") may be imaged onto the target retinal image TRI (FIG. 2 section "a"), as a rectangular area 42, and this area 42 repetitively scanned across the target retinal image TRI—as indicated by the arrows 43. If the detector sensitive-area image 42 is reasonably narrow in relation to the widths of the lines 41 (preferably narrower than illustrated), the scanning process will produce a fairly deep trapezoidal-wave signal from the detector D.

The depth, the sharpness of the corners, and the steepness of the nonhorizontal portions of this trapezoidal waveform will all increase with the sharpness of focus of the target retinal image TRI on the retina. In this way the sharpness of the focus is translated into amplitude of an a. c. signal from the detector D. Alternatively other features of the waveform, such as the rate of change of the detector output (the derivative of the output signal) per unit scanning speed, may be used as an indicator of the sharpness of focus.

In any of these cases, in order to avoid the "confusion" caused by the fact that both too-short focus and too-long focus produce similar blurring, the apparatus may have two discrete detectors, and the scanner may automatically scan the sensitive areas of both detectors across the target retinal image TRI simultaneously—but with two slightly different focal lengths respectively. When the target retinal image TRI is most sharply focused, the two detector signals corresponding to the two focal lengths will have the same a. c. amplitude, the same detector-output derivative per unit scanning speed, etc.

The orientation and scan direction of the detector sensitive-area image 42' should be arranged to track the orientation of the target retinal image TRI', so that the long dimension (if any) of the sensitive-area image 42'0 is parallel to the lines 41' and the scan direction 43' is perpendicular to the lines 41'.

As shown in FIG. 3, the relationship between displacement x of the target T, T' (sections "a" and "b" of FIG. 1) and the optical power of the eye lens EL, EL' is very nearly linear. Thus to a close approximation the readings from the indicator pointer 136 against the scale 137 are proportional to changes in optical power, for a restricted range of change of power.

It will be understood that the foregoing disclosure is intended to be merely exemplary, and not to limit the scope of the invention—which is to be determined by reference to the appended claims.

I claim:

1. A method of obtaining information related to blood-glucose concentration in a living subject, comprising the steps of:
    obtaining a test measure of the optical power of at least one eye of such subject; and
    then comparing the test measure with a calibration measure of optical power that corresponds to a reference blood-glucose level in such subject, to obtain such glucose-related information.

2. The method of claim 1, further comprising the steps of:
    before the test-measure-obtaining step, obtaining the calibration measure of optical power; and
    substantially contemporaneously with the calibration-measure-obtaining step, determining the reference blood-glucose level in such subject.

3. The method of claim 2, wherein:
    the determining step comprises analysis of the patient's blood.

4. The method of claim 1, wherein:
    the comparing step comprises noting whether the test measure is higher or lower than the calibration measure; and
    such glucose-related information comprises the conclusion that such patient's blood glucose level is, respectively, higher or lower than the reference level.

5. The method of claim 1, wherein:
    the reference level is unhealthfully high;
    the comparing step comprises noting whether the test measure is or is not lower than the calibration measure; and
    such glucose-related information comprises the conclusion that such patient's blood-glucose level is or is not, respectively, improved relative to the unhealthfully high reference level.

6. The method of claim 1, wherein:
    the comparing step comprises comparing the test measure with a plurality of calibration measures of optical power that correspond to a respective plurality of reference blood-glucose levels in such subject; and
    such glucose-related information comprises an estimate of blood-glucose concentration in such subject, calculated from the plurality of calibration measures, the corresponding plurality of reference levels, and the test measure.

7. The method of claim 1, wherein the test-measure-obtaining step comprises:
    projecting an image through an external optical system, and through the cornea and lens of such subject's eye onto such subject's retina;
    during the projecting step, monitoring the sharpness of focus of the image on such subject's retina;
    during the monitoring step, modifying the conditions of projection of the image and determining the relationship between the projection conditions and the sharpness of focus; and
    using the relationship to obtain the test measure.

8. The method of claim 7, particularly adapted for such subjects who are presbyopic, and wherein:
    the external optical system has adjustable optical power, and has means for indicating the value of optical power to which the system is adjusted;
    the modifying and determining step comprises adjusting the optical power of the external optical system to focus the image on such subject's retina as sharply as possible, and while the optical power is so adjusted reading the optical power of the external system from the indicating means; and
    the using step comprises using the power so read as the test measure.

9. The method of claim 7, particularly adapted for such subjects who are presbyopic, and wherein:
the image is an image of an object that is at an adjustable effective distance from such subject's eye;
the external optical system comprises means for indicating the effective distance to which the object is adjusted;
the modifying and determining step comprises adjusting the effective distance of the object to focus the image on such subject's retina as sharply as possible, and while the effective distance is so adjusted reading the effective distance from the indicating means; and
the using step comprises using the distance so read as the test measure.

10. The method of claim 1, particularly adapted for such subjects who are substantially not presbyopic, and wherein:
the test-measure-obtaining step is performed at the far point for such eye.

11. The method of claim 1, particularly adapted for such subjects who are substantially not presbyopic, and wherein:
the test-measure-obtaining step is performed at the near point for such eye.

12. The method of claim 2, particularly adapted for such subjects who are substantially not presbyopic, and wherein:
the test-measure-obtaining step is performed at the near point for such eye and comprises:
projecting an image of an object through the cornea and lens of such subject's eye onto such subject's retina from an external optical system whose optical power is preadjusted to focus such subject's eye at a relatively large distance when the eye muscles are relaxed and when such subject's blood-glucose concentration is substantially at said reference level;
during the projecting step, monitoring the sharpness of focus of the image on such subject's retina;
during the monitoring step, progressively changing the position of the object, from a starting position which to such subject appears at a relatively large distance, toward subsequent closer positions;
determining the closest position at which sharpness of focus of the image on such subject's retina is maintained; and
using said closest position as the test measure of optical power at the near point.

13. The method of claim 7, wherein:
the monitoring step is performed by means of such subject's own visual sensation of the image on the retina.

14. The method of claim 9, wherein:
the monitoring step is performed by means of such subject's own visual sensation of the image on the retina.

15. The method of claim 12, wherein:
the monitoring step is performed by means of such subject's own visual sensation of the image on the retina.

16. The method of claim 13, wherein:
such subject performs the projection-condition modifying step.

17. The method of claim 14, wherein:
such subject performs the optical-power adjusting step.

18. The method of claim 15, wherein:
such subject performs the effective-object-distance adjusting step.

19. The method of claim 13, wherein:
the image is an image of the retina of a particular one of such subject's own eyes; and
the projecting step comprises illuminating the retina of that particular eye to project an image of that retina outward through the lens and cornea of that particular eye to the external optical system, for projection through the external optical system and onto the retina recited in claim 13.

20. The method of claim 7, wherein:
the projecting step comprises projecting an image that has an intensity gradient;
the monitoring step comprises automatically scanning the image of a photoelectric detector along the gradient.

21. Apparatus for obtaining information related to blood-glucose concentration in a living subject who has at least one eye that includes a lens and a retina; said apparatus comprising:
means for projecting, under adjustable projection conditions, an image of an object through an external optical system and through such eye lens onto such retina;
means for adjusting the projection conditions of the external optical system in response to the optical power of said eye; and
an indicator, responsive to the adjusting means and graduated in units of blood-glucose concentration, for indicating the approximate blood-glucose concentration in such subject that corresponds to the projecton conditions of the external optical system.

22. Apparatus for obtaining information related to blood-glucose concentration in a living subject who has at least one eye that includes a lens and a retina; said apparatus comprising:
means for projecting, under adjustable projection conditions, an image of an object through an external optical system and through such eye lens onto such retina;
means for adjusting the projection conditions of the external optical system; and
an indicator, responsive to the adjusting means and graduated in units of blood-glucose concentration, for indicating the approximate blood-glucose concentration in such subject that corresponds to the projection conditions of the external optical system wherein the adjustable projection conditions comprise the optical power of the external optical system.

23. Apparatus for obtaining information related to blood-glucose concentration in a living subject who has at least one eye that includes a lens and a retina; said apparatus comprising:
means for projecting, under adjustable projection conditions, an image of an object through an external optical system and through such eye lens onto such retina;
means for adjusting the projection conditions of the external optical system; and
an indicator, responsive to the adjusting means and graduated in units of blood-glucose concentration, for indicating the approximate blood-glucose concentration in such subject that corresponds to the projection conditions of the external optical system wherein the adjustable projection conditions comprise the effective distance of the object from such eye lens.

24. Apparatus for obtaining information related to a blood-glucose concentration in a living subject who has at least one eye that includes a lens and a retina; said apparatus being paritcularly adapted for such subjects that are presbyopic, said apparatus comprising:
means for projecting, under adjustable projection conditions, an image of an object through an external optical system and through such eye lens onto such retina;
means for adjusting the projection conditions of the external optical system;
an indicator, responsive to the adjusting means and graduated in units of blood-glucose concentration, for indicating the approximate blood-glucose concentation in such subject that corresponds to the projection conditions of the external optical system;
automatic means for sensing sharpness of focus of the image on such retina;
means responsive to the automatic sensng means, for controlling the adjusting means to maximize the sharpness; and
whereby the apparatus automatically focuses the image on such retina to maximum sharpness and indicates the blood-glucose concentration level in such subject that corresponds to the power of the external optical system.

25. Apparatus for obtaining information related to blood-glucose concentration in a living subject who has at least one eye that includes a lens and a retina; said apparatus being particularly adapted fro such subjects that are presbyopic, said apparatus comprising:
means for projecting, under adjustable projection conditions, an image of an object through an external optical system and through such eye lens onto such retina;
means for adjusting the projection conditions of the external optical system; and
an indicator responsive to the adjusting means and graduated in units of blood-glucose concentration, for indicating the approximate blood-glucose concentration in such subject that corresponds to the projection conditions of the external optical system and wherein:
the adjusting means are manually adjustable by such living subject; and
the sharpness of focus of the image on such retina is perceptible by such subject's own visual sensation of the image on such retina;
whereby such subject can focus the image on such retina to maximum sharpness and can read from the indicator such subject's own blood-glucose concentration level that corresponds to the power of the external optical system.

26. The apparatus of claim 23, further comprising:
automatic control means for controlling the adjusting means to progressively vary the effective object distance from a relatively long distance toward a relatively short distance;
automatic means for sensing sharpness of focus of the image on such retina; and
automatic means, responsive to both the automatic control means and the automatic sensing means, for causing the indicator means to indicate the blood-glucose concentration that corresponds to the shortest effective object distance at which a substantially sharp focus is sensed by the automatic sensing means.

27. The apparatus of claim 23, further comprising:
manually manipulable control means for use, by such subject or by an assistant, in controlling the adjusting means to progressively vary the effective object distance from a relatively long distance toward a relatively short distance;
automatic means for sensing sharpness of focus of the image on such retina; and
automatic means, responsive to both the manually manipulable control means and the automatic sensing means, for causing the indicator means to indicate the blood-glucose concentration that corresponds to the shortest effective object distance at which a substantially sharp focus is sensed by the automatic sensing means.

28. The apparatus of claim 23, further comprising:
manually manipulable control means for use, by such subject or by an assistant, in controlling the adjusting means to progressively vary the effective object distance from a relatively long distance toward a relatively short distance;
whereby such subject, while perceiving by such subject's own visual sensation the degree of sharpness of focus of the image on such retina, can cause the manually controlled progressive variation of effective object distance to be halted when such subject perceives that the image is not substantially sharp; and
whereby the indicator means can be read to obtain the blood-glucose concentration that corresponds to the shortest effective object distance at which the subject perceives a substantially sharp focus.

29. The apparatus of claim 21, wherein: the external optical system comprises a spectacle lens that is particularly adapted to:
correct such subject's vision, including astigmatism if present, and
focus such subject's eye at a relatively large distance,
when the eye muscles are relaxed and when such subject's blood-glucose concentration is at a predetermined reference level.

30. The apparatus of claim 29, wherein: the relatively large distance is infinity.

31. Apparatus for obtaining information related to blood-glucose concentration in a living subject who has at least one eye that includes a lens and a retina; said apparatus being particularly for use if such subject's eye has glycemia-induced astigmatism and such astigmatism is characterized by an axis meridian, and comprising:
means for projecting, under adjustable projection conditions, an image of an object through an external optical system and through such eye lens onto such retina;
the image of said object on such retina including a plurality of parallel lines that are aligned substantially perpendicular to the axis meridian of glycemia-induced astigmatism in such subject's astigmatic eye;
means for adjusting the projection conditions of the external optical system in response to the optical power of said eye; and
an indicator, responsive to the adjusting means, for providing as indication related to the projection conditions of the external optical system;

whereby the indicator provides an indication related to the approximate blood-glucose concentration in such subject that corresponds to the projection conditions; and whereby sharpness of focus of the image onto such retina is substantially independent of glycermia-induced astigmatism exceeding that which corresponds to said predetermined blood-glucose reference level.

32. Apparatus for obtaining information related to blood-glucose concentration in a living subject whose has at least one eye that includes a lens and a retina; said apparatus being particularly for use with such subjects whose eye-pupil dilation capability is substantially normal to at least well beyond five-millimeter pupil diameter, and comprising:

means for projecting, under adjustable projection conditions, an image of an object through an external optical system and through such eye lens onto such retina, said image appearing on a field, and said image and field being characterized by brightness;

means for adjusting the brightness of the image to a level that causes the pupil diameter of such subject's eye to be approximately five millimeters;

means for adjusting the projection conditions of the external optical system in response to the optical power of said eye; and an indicator, responsive to the adjusting means, for providing an indication related to the projection conditions of the external optical system;

whereby the indicator provides an indication related to the approximate blood-glucose concentration in such subject that corresponds to the projection conditions; and whereby the relationship between said indication and such glucose concentration has a sensitivity that is substantially optimized for depth of field and aberrations.

33. The apparatus of claim 32, wherein:

the object is illuminated at roughly two to ten candelas per square meter.

* * * * *